United States Patent [19]

Chapelon et al.

[11] Patent Number: 5,720,286
[45] Date of Patent: Feb. 24, 1998

[54] USE OF A-MODE ECHOGRAPHY FOR MONITORING THE POSITION OF A PATIENT DURING ULTRASOUND THERAPY

[75] Inventors: Jean-Yves Chapelon, Villeurbanne; Emmanuel Blanc, St. Genis Laval, both of France

[73] Assignees: Technomed Medical Systems, Vaulx en Velin; Institut National de la Sante et de la Rcherche Medicale, Paris, both of France

[21] Appl. No.: 451,914

[22] Filed: May 26, 1995

[30] Foreign Application Priority Data

May 30, 1994 [FR] France ................... 94 06539

[51] Int. Cl.$^6$ ......................................... A61B 8/00
[52] U.S. Cl. .................... 128/660.03; 128/662.06
[58] Field of Search .......... 128/660.03, 660.02, 128/662.06, 660, 661.06; 601/4

[56] References Cited

U.S. PATENT DOCUMENTS

| | | | |
|---|---|---|---|
| 4,819,621 | 4/1989 | Ueberle et al. | 601/4 |
| 4,991,604 | 2/1991 | Wurster et al. | 128/660.03 |
| 5,036,855 | 8/1991 | Fry et al. | 128/660.03 |

FOREIGN PATENT DOCUMENTS

WO9115154  10/1991  France .
WO9312742  7/1993  France .
WO9317646  9/1993  Germany .

OTHER PUBLICATIONS

IEEE Transactions on Sonics and Ultrasonics, Ultrasonic Hyperthermia for Ophthalmic Therapy, vol. 31, No. 5, Sep. 1984, pp. 473–481. Rapport De Recherche Preliminaire (Completion date Jan. 23, 1995).
International Search Report (Completion date Apr. 14, 1993).
International Search Report (Completion date Jul. 23, 1991).
International Search Report (Completion date Sep. 3, 1993).

*Primary Examiner*—Marvin M. Lateef
*Assistant Examiner*—Derrick Fields
*Attorney, Agent, or Firm*—Welsh & Katz, Ltd.

[57] ABSTRACT

An A-mode ultrasound echography method is employed for monitoring the position of a patient during hyperthermia treatment. A therapy apparatus includes a therapy device having at least one ultrasound therapy transducer and at least one monitoring ultrasound transducer, where the ultrasound monitoring transducer is linked to an electronic circuit for processing A-mode signals and is part of an A-mode echography device. The therapy apparatus further includes a device for causing the ultrasound transducer operating in A-mode to transmit a brief signal and to receive the echo of the brief signal. A comparing device compares the echo received with a reference echo, and transmits the result of the comparison to a control device.

34 Claims, 6 Drawing Sheets

USE OF A-MODE ECHOGRAPHY FOR MONITORING THE POSITION OF A PATIENT DURING ULTRASOUND THERAPY

BACKGROUND OF THE INVENTION

This invention essentially relates to the use of an ultrasound echography device operating in A-mode for monitoring the position of a patient during a therapy session, and to a method and apparatus applying it.

It is known that focused ultrasound can be used for treating tumors. Generally, this is done in several stages, and more specifically consists in first locating the volume to be treated, then calculating the firing positions and after this directing successive shots to the calculated positions.

In accordance with known methods, the shot is either done "blind" or sometimes advantage is taken of the vacant period between shots for providing an ultrasound image for monitoring purposes.

Treatment that is done "blind" can be dangerous as the sessions are frequently long and the patient—even if anesthetized—may well move. In this case, there is a danger of damaging healthy or even vital parts.

Thus, by providing an image, the actual position of the therapeutic transducer with respect to organs close to the target can be monitored. However, this method does not offer absolute safety as one cannot be sure that the medical personnel will pay sustained attention to the screen displaying the ultrasound image throughout the whole duration of the treatment. Image analysis techniques have been proposed in order to overcome this disadvantage but these require specific and highly complex electronic systems and software which increases the cost of equipment and can be the source of additional problems.

Another disadvantage of this solution resides in the actual ultrasound scan itself. The system used may be conventional in the sense that it includes an ultrasound scanning head as described in International application WO 92/15253. This document discloses the incorporation of an ultrasound scanning head into a therapy transducer, but this means that the head masks a portion of the therapy transducer thus reducing the effectiveness of the apparatus, as is pointed out in said application where it is indicated that one always attempts to maximize the transmission surface area of the therapy transducer.

It is also possible to obtain an ultrasound image of the target and the area surrounding it without reducing the transmission surface area of the therapy transducer. This is achieved by using a transducer element connected to B-type scan apparatus as described in IEEE 1992 Ultrasonics Symposium Proceedings, in an article by N. T. Sanghvi, R. S. Foster, F. J. Fry, R. Birhle, C. Hennige and L. V. Hennige entitled "Ultrasound intracavitary system for imaging, therapy and planning, and treatment of focal diseases", pages 1,249 to 1,253. For each position of the therapy transducer head, one line of the image will be obtained. In order to obtain the complete image, it is thus necessary to move the therapy head sequentially. This is a slow process as the image rate is limited by the mechanical scanning of the therapy head.

Moreover, before it was known how to produce an image with B-mode scanning equipment, A-mode echography was employed either for measuring distance, for example in echography of the eye, or for measuring the degree of opening of mitral valves, or, yet again, for measuring and locating the mid-axis of the brain, or, still further, for bone positional location with a view to treatment as described in an earlier document in the name of the assignee, FR-A-2, 660,186 equivalent to U.S. Pat. No. 5,235,981.

However, A-mode echography has never been employed at the actual time of therapy and even less for monitoring the position of a patient during therapy.

Additionally, to check the position of a patient during therapy, the use of luminous markers has been proposed: see FR-A-2,663,529 in the name of the present assignee; U.S. Pat. No. 4,132,900 (W. E. Smith); DE-A-2,361,155 (C. Lescrenier) and EP-A-0,260,550 (Siemens A. G.). However, luminous markers can obviously not be employed in certain cases, as is for example the case in endocavital treatment.

SUMMARY OF THE INVENTION

The present invention thus sets out to resolve the technical problem of supplying a way of reliably and accurately monitoring the position of a patient during therapy. It would be advantageous if this solution could be particularly simple.

A further aim of the invention is to provide a way of supplying an image allowing the position of a patient to be automatically monitored during therapy in a reliable, accurate and particularly simple fashion.

A further aim of the invention is to provide a way of not only monitoring the position of a patient during therapy, but also of performing correction and closed-loop control of the position either of the patient or of the therapy apparatus during therapy, so that said therapy may be correctly performed throughout the whole duration thereof. Preferably, this solution should also enable real time control of a therapy transducer to be obtained with respect to a predetermined reflecting contour, this being done independently of all other traditional imaging systems.

Yet a further aim of the invention is to resolve the above technical problems while at the same time providing a way of alerting the practitioner and/or medical staff during therapy should the patient's position inadvertently change.

This invention makes it possible to simultaneously resolve all the technical problems stated above in a safe and reliable manner that can be applied on an industrial and medical scale.

Thus, according to a first aspect, the invention provides for the use of an A-mode echography device for monitoring the position of a patient, during a therapy session.

When A-mode echography is used in this way, it is advantageous to modify the aim of the therapy apparatus as a function of movements detected by the A-mode echography device.

It can also be arranged for the A-mode echography device to interrupt therapy if it is detected that movements of the patient are above a predefined limit which may be a function of a safety margin.

According to one preferred feature, the A-mode echography device carries out real time control of the position of therapy apparatus comprising, for example, a therapy probe with respect to a predetermined reflecting contour, preferably independently of any other conventional imaging system, this being particularly simple.

For example, to take the example of treatment of the prostate, it is possible to control the therapy device which for example includes at least one therapy transducer, using the A-type echo from the rectal wall. This is performed independently of the imaging system. This makes it possible to create lesions situated at a precise distance, typically some 3 mm, from the rectum, for correct treatment. Similarly, in the case of thyroid treatment, provision can also be made to control the therapy device in real time on the basis of the echo from the trachea.

For the actual therapy, therapy apparatus using focused ultrasound is preferably employed.

According to a second aspect, this invention also provides a method for monitoring the position of a patient, in particular the position of an organ of the patient to be treated, during a therapy session including:

a) providing an ultrasound monitoring transducer operating in A-mode in acoustic contact with the patient to be monitored, in particular with an organ to be treated, the transducer being in a known position, for example fixed to a structure which, in particular, is the supporting means for said patient;

b) exiting the ultrasound monitoring transducer operating in A-mode with a brief signal in the form of a pulse, for example between shots of an apparatus providing said therapy;

c) receiving the echoes of the signal at the transducer;

d) transforming said received echoes into an electrical signal;

e) locating, in the signal corresponding to the echoes, the position or shape of a structure that is characteristic of the echo from a tissue to be monitored of the patient;

f) comparing the position or shape of the structure characteristic of the echo from a tissue to be monitored in the patient with the position or shape of a reference echo signal from tissue to be monitored of said patient; and g) when the result of the comparison indicates a change of the position or shape of the received echo signal with respect to the reference echo signal position or shape, transmitting this information to an appropriate control device.

According to an advantageous feature, the control device triggers an alarm when information is transmitted thereto indicating a change in the position or shape of the echo signal received with respect to a reference echo signal, or even the absence of reception of said echo signal.

Advantageously, the control device performs real time closed-loop control of the position of the therapy device as a function of the movements of the patient, in particular of said organ to be treated, preferably with respect to a predetermined reflecting contour of said patient such, as the rectal wall during prostate treatment, or the trachea during thyroid treatment.

According to a further advantageous feature, the ultrasound monitoring transducer operating in A-mode is mechanical linked to the therapy device.

The therapy device preferably includes at least one ultrasound therapy transducer providing therapy using focused ultrasound.

The ultrasound therapy transducer is advantageously arranged inside balloon means filled with an acoustic coupling fluid.

Preferably, the reference echo signal corresponds to the desired distance between a highly echogenic interface, such as the interface in contact with the wall of the balloon means and the ultrasound therapy transducer, the comparison consisting of comparing the actual distance measured for the echo corresponding to said interface and the reference distance for the interface relative to said therapy transducer.

According to a preferred feature, when the measured distance is smaller than the reference distance, the therapy transducer is controlled whereby its distance with respect to the patient, in particular with respect to an organ to be treated increases, while if the measured distance is greater than said reference distance, the therapy transducer is controlled whereby its distance with respect to the patient, and in particular with respect to the organ to be treated, is decreased.

The ultrasound therapy transducer is preferably a focused ultrasound therapy transducer integrated into an endocavital probe, preferably a rectal probe, for providing treatment of benign or malignant tumors, in for providing treatment of the prostate or the thyroid, notably cancers.

Other advantageous embodiments will also become evident from the detailed description provided below that relates to the therapy apparatus and from the examples and the drawings which constitute an integral part of this disclosure.

According to a third aspect, the invention provides a therapy apparatus including a therapy device including at least one ultrasound therapy transducer and at least one monitoring ultrasound transducer, wherein said ultrasound monitoring transducer is linked to an electronic circuit for processing A-mode signals and constituting part of an A-mode echography device, the therapy apparatus further including means for causing the ultrasound transducer operating in A-mode to transmit a brief signal and receive the echo of the brief signal at the A-mode transducer, means for comparing the echo received with a reference echo, and means for transmitting the result of the comparison to a control device.

According to one advantageous feature, the control device triggers alarm means.

The control device advantageously performs real time closed-loop control of the position of the therapy transducer relative to the patient and in particular, relative to the organ to be treated.

Advantageously, the ultrasound therapy transducer is of the focused type.

According to one preferred feature, both the ultrasound therapy transducer and the A-mode monitoring transducer are integrated into an endocavital probe, in particular a rectal endocavital probe.

In an advantageous embodiment, the focused-type therapy transducer is linked to means for supplying an electronic signal providing variable focusing. The control device preferably provides closed-loop control of the focal length of said therapy transducer as a function of the movements of the patient during the course of therapy.

The therapy apparatus preferably includes means for continuously recording the echoes created by the monitoring transducer operating in A-mode. The A-mode electronic circuit may include an echography device operating in A-mode.

Other advantageous embodiments will also become evident from the description that follows that relates to the therapy apparatus and from the examples and drawings which constitute an integral part of this disclosure.

It will be seen that the invention makes it possible to monitor the position of a patient during therapy in a simple, accurate and reliable fashion, thus resolving the technical problems discussed above, as well as providing other technical advantages which will be evident to those skilled in the art.

DETAILED DESCRIPTION OF PREFERRED EMBODIMENTS

Figure 1:
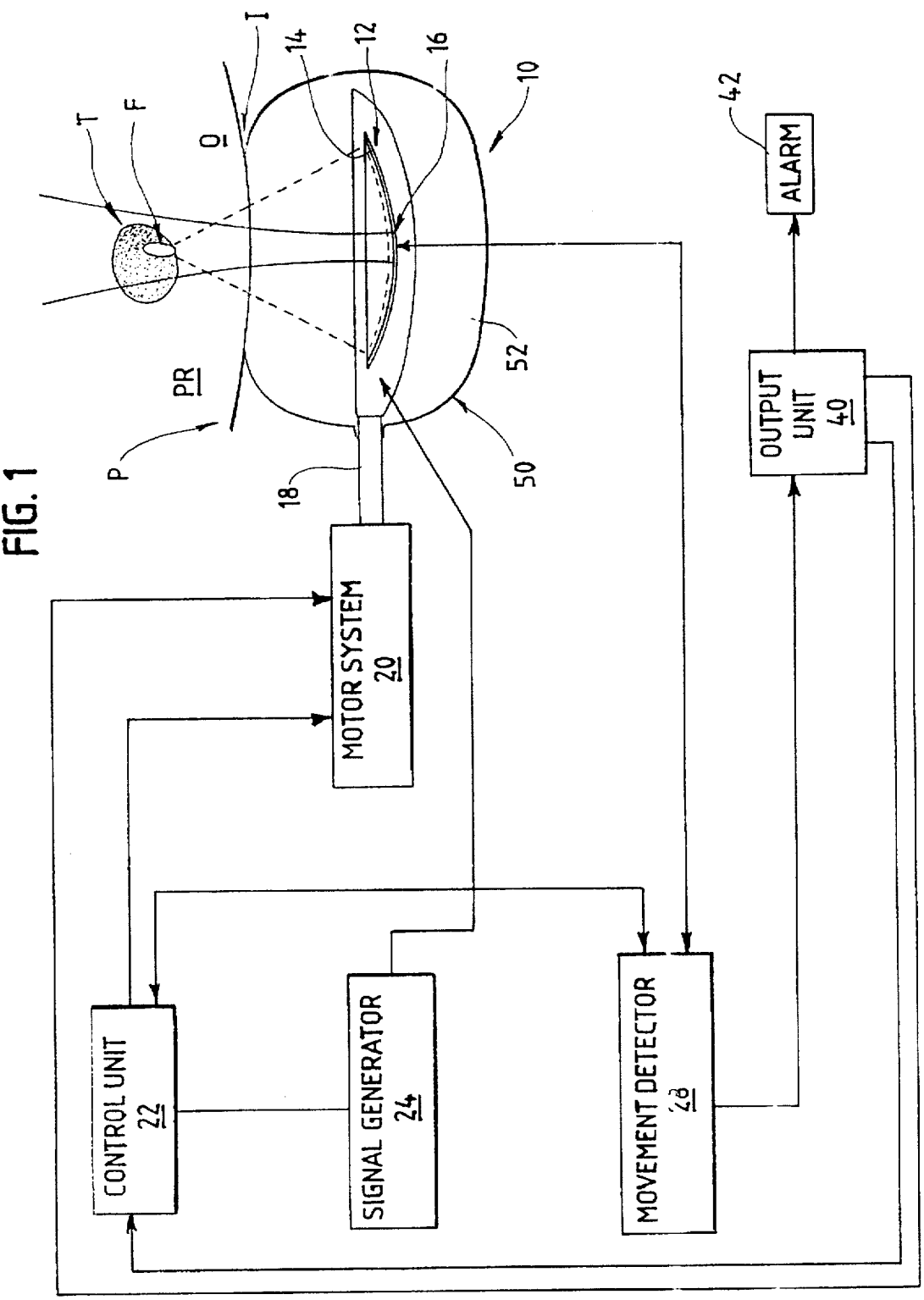
FIG. 1 is a diagrammatical view of a first embodiment of the therapy apparatus according to the invention, showing the actual therapy device which here takes the form of a rectal endocavital transducer with an A mode monitoring transducer, in longitudinal cross-section, together with essential control and detection means.

With reference to FIGS. 1 to 4, the therapy apparatus according to the present is generally identified by the reference numeral 10. The therapy apparatus includes an actual therapy device generally indicated by reference numeral 12, including a therapy transducer 14 which here takes the form of a naturally focusing cup-shaped dish, together with at least one ultrasound monitoring transducer 16 linked to an electronic circuit for A-mode echography. Those skilled in the art will readily recognize that the transducer 16 can constitute part of an A-mode echography device.

In one preferred embodiment, the active part of ultrasound monitoring transducer 16 is an integral part of therapy transducer 14 and thus does not constitute a transducer separate from the latter, although such an alternative embodiment would also be possible.

The monitoring element can be situated at the center of the transducer, on its axis of symmetry.

The monitoring transducer can be obtained by partitioning the metal film deposited on the piezo-electric material forming the therapy transducer and designed to stimulate it electrically. This method is an easy way of obtaining two piezo-acoustic elements able to be controlled separately. The partitioning of the metallization layer can be arranged so that the monitoring element has minimal surface area so that there is only a very slight reduction of useful surface of the element used for therapy.

In an advantageous embodiment, therapy device 12 may take the form of an endocavital probe 18 of the type described in WO 92/15253 which is incorporated herein by reference.

In particular, and also in accordance with this earlier document, the rear part of endocavital probe 18 may include a motor system 20 enabling endocavital probe 18 to be driven in translation and/or rotation so that the endocavital probe can be accurately positioned facing a target T requiring treatment, such as a tumor inside an organ O, for example the prostate PR, defined by a surface forming an interface I of patient P. The same references are employed in the embodiments of FIGS. 4 to 6.

Figure 2:
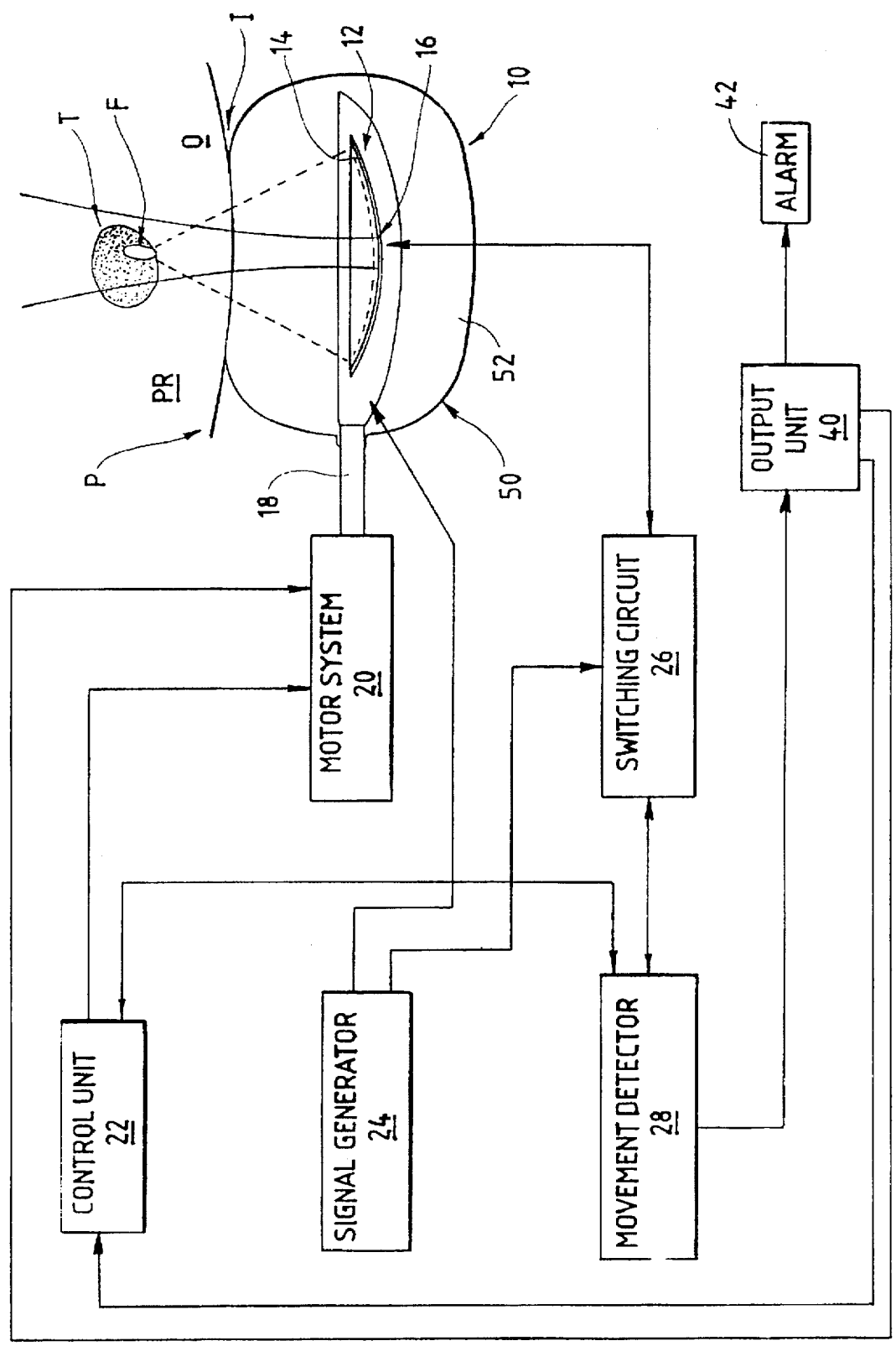
FIG. 2 is an alternative embodiment of the device shown in FIG. 1.

The therapy apparatus also includes a control unit 22 which is not only responsible for controlling the motor means 20 providing translatory and/or rotational movement for endocavital probe 18, but also for controlling an electronic signal generator 24 which in turn controls the operation of therapy transducer 14 and/or monitoring transducer 16 via an electronic movement detector 28, the structure of which is described in more detail with reference to FIG. 3. A switching circuit 26 as shown in FIG. 2 (in conjunction with electronic movement detector 28) can be provided.

Figure 3:
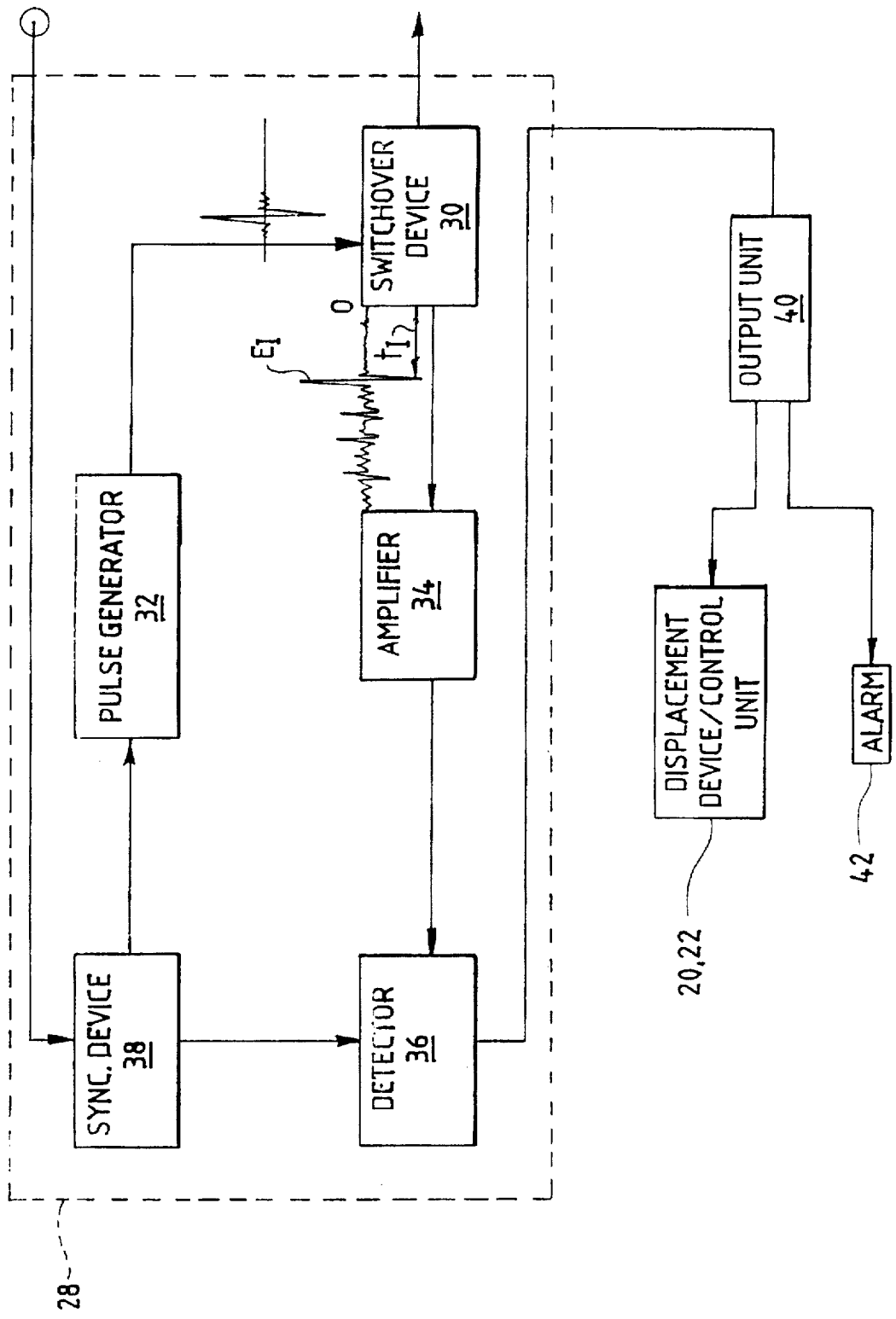
FIG. 3 shows the movement detection circuit in greater detail.

FIG. 3 shows the internal structure of the movement detector 28. Monitoring transducer 16 can be linked, via a transmit/receive switchover device 30, either to a pulse generator subassembly 32 or to a signal processing subassembly including an amplifier 34 and a detector 36. Both subassemblies are synchronized by a synchronization device 38 triggered by a signal from control unit 22. The processing subassembly 34, 36 analyzes the echo received by monitoring transducer 16 and generates a control signal for an output unit 40 which can take the form of alarm generating means or means for driving the translatory and/rotational displacement means 20 for endocavital probe 18, optionally via control unit 22.

Figure 4:
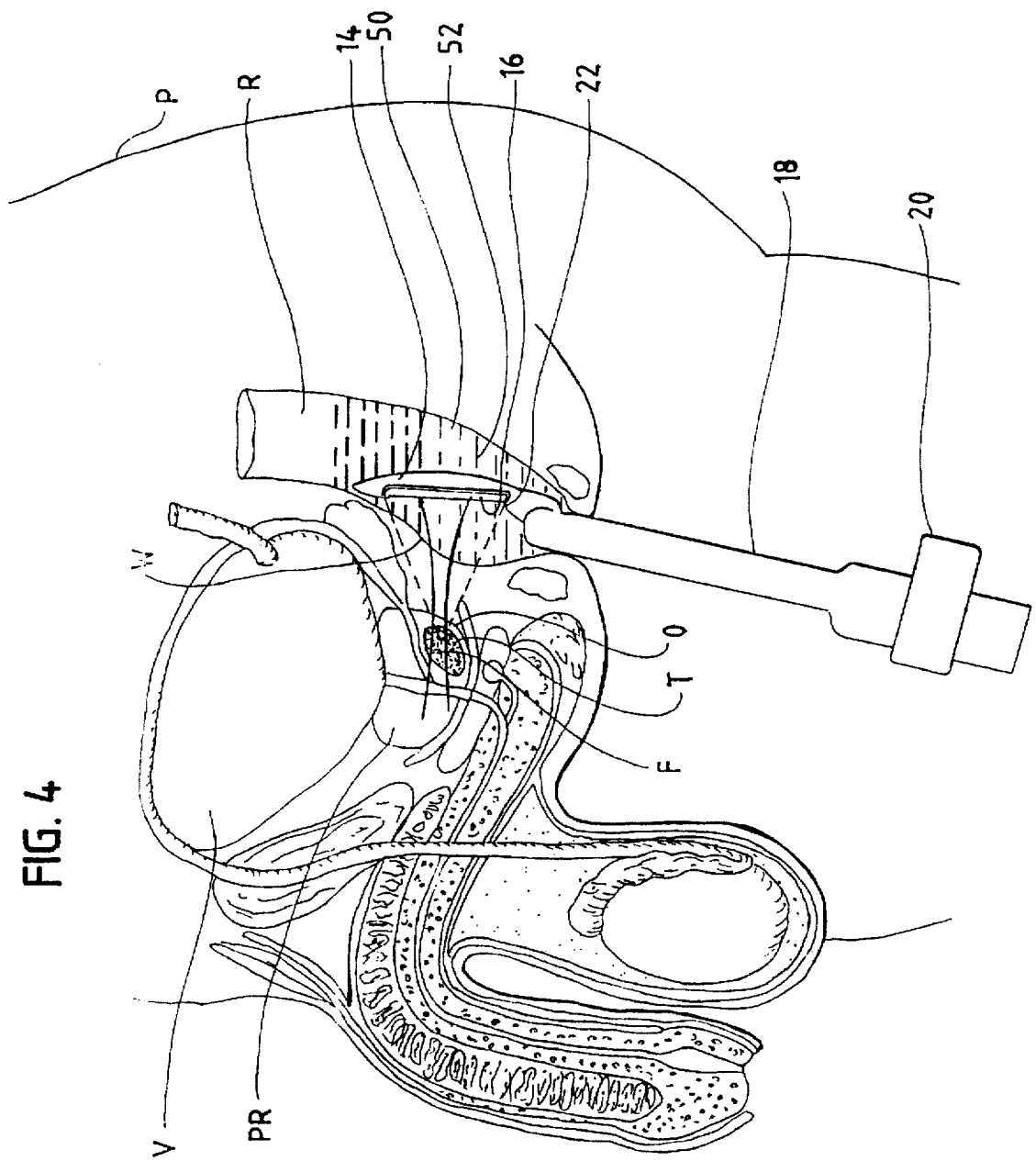
FIG. 4 shows a second embodiment of a therapy apparatus according to this invention which here takes the form of a therapy device with a rectal endocavital transducer for treating the prostate, in the working position, inside a bag or balloon filled with an acoustic coupling fluid, the surface of the bag or balloon being in contact with the organ to be treated.
Figure 5:
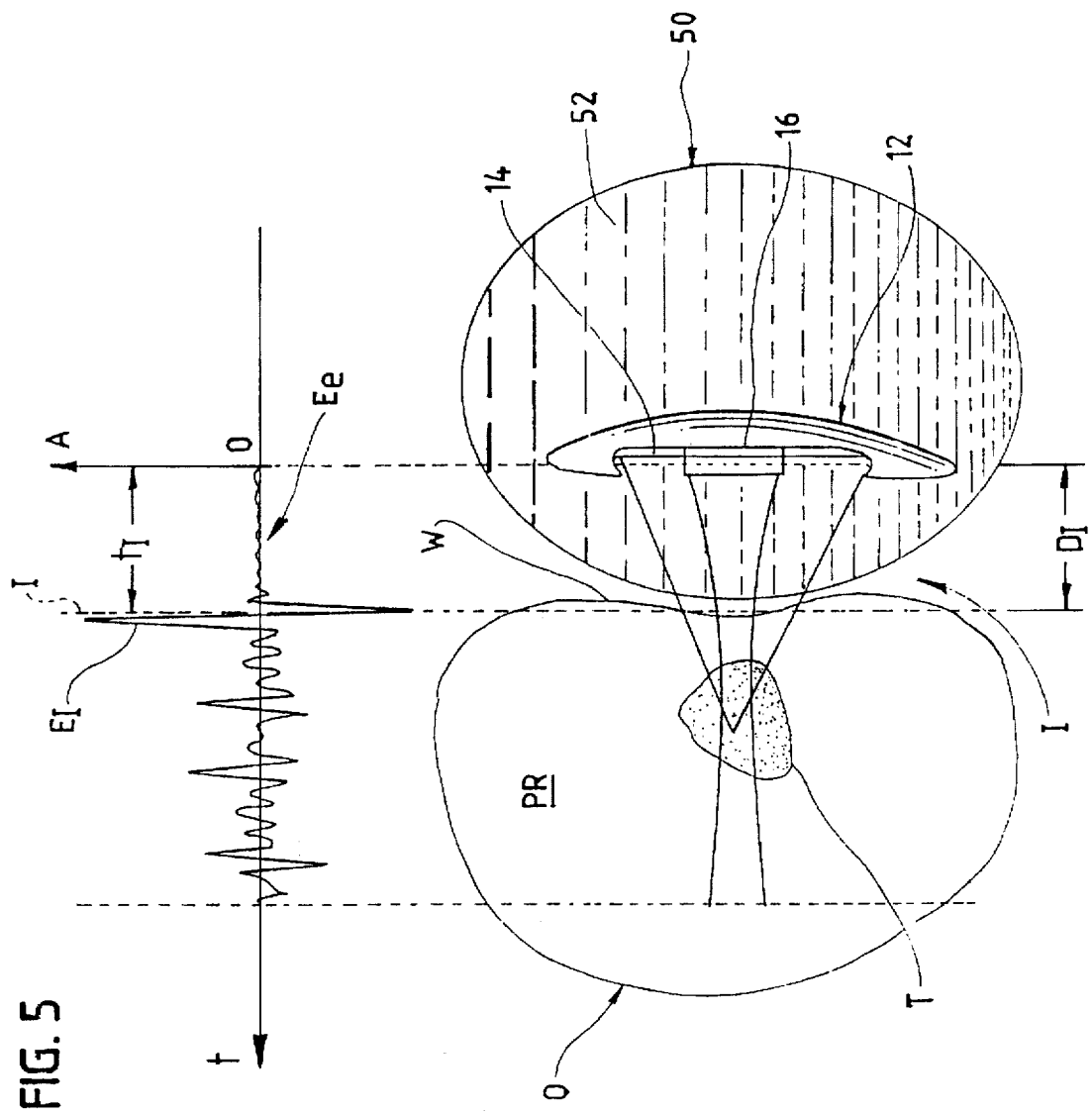
FIG. 5 shows the therapy device coupled to the A-mode ultrasound monitoring transducer of FIG. 4, on a larger scale, with the echo signal received by the A-mode transducer following transmission of a short pulse signal making it possible to observe the shape and structure of the echo pulse corresponding to an interface being monitored, which here is the rectal wall.
Figure 6:
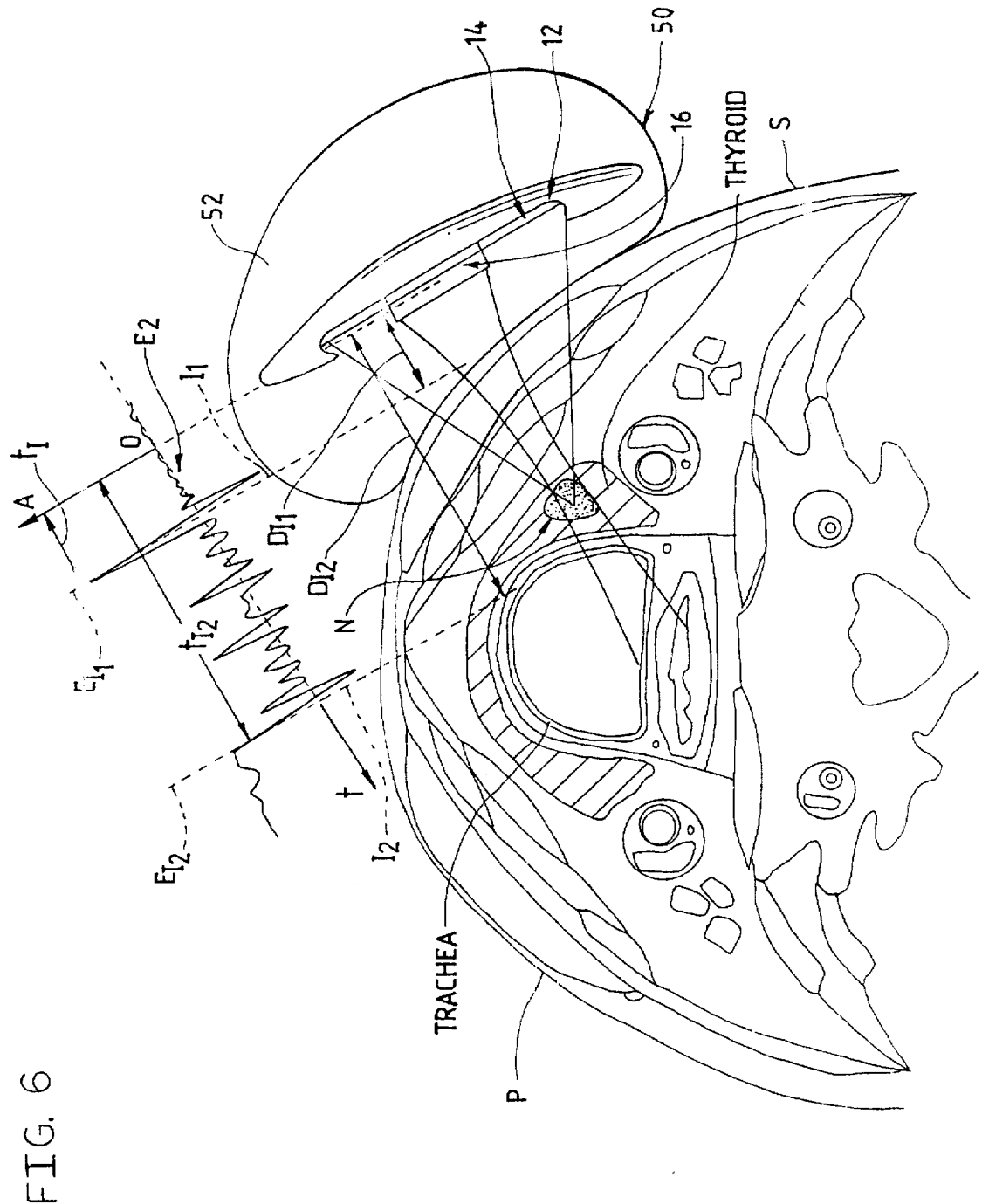
FIG. 6 shows a third embodiment of therapy apparatus according to the invention, the therapy device taking the form of an extracorporeal probe in the form of a cup-shaped focusing dish—here for treating the thyroid—showing a horizontal section passing through the thyroid.

The operation of the treatment apparatus of this invention will become more clear from the two examples of treatment illustrated in FIGS. 4 to 6.

Referring now to FIGS. 4 to 6, it will first be observed that therapy transducer 14 is delivering a beam focused to focal region F which here has been shown diagrammatically as having an approximately triangular shape which, for good therapy, should be situated at or within the target zone to be treated, such as a tumor T inside an organ O which may for example be the prostate, as will be described with reference to FIG. 4, or the thyroid, as will be described with reference to FIG. 6.

In the embodiment shown in FIGS. 1 to 6, the monitoring transducer 16 operating in A-mode is integrated into therapy transducer 14 and, for example, occupies the central portion thereof as can be clearly seen in FIGS. 2 and 4 to 6.

In an advantageous embodiment, therapy transducer 14 integrating the monitoring transducer 16 can be manufactured from a composite material as described in an earlier French patent application in the name of Technomed International FR-A-2,679,125 which is incorporated herein by reference.

It is also possible as shown in FIG. 2, to employ the central element of the transducer for both monitoring and therapy purposes- In this case, a switching circuit 26 FIG. 2 is used to successively link the central element to an electronic power signal generator 24 or to movement detector 28.

The same central transducer can also be employed for tissue characterization purposes prior to, during and after treatment. In this mode, the return echoes are analyzed in order to determine the structure of the treated tissue or the effect of treatment itself.

Monitoring transducer 16 transmits an A-mode signal the beam shape of which is shown on each of FIGS. 1, 2, 4, 5 and 6. In the framework of this invention, it is preferable for the beam from A-mode monitoring transducer 16 to cover the focal region F so that this region can also be monitored during treatment. However, with respect to monitoring the position of the patient, in particular organ O, it is not absolutely essential for the beam from monitoring transducer 16 operating in A-mode to pass through the focal region, as the essential purpose of the monitoring transducer is to monitor the position of a highly echogenic surface which will generally consist of the interface I of the trachea of patient P, as will be described with reference to FIG. 6, or the wall of the organ O to be treated, for example the prostate PR as shown in FIGS. 1, 2, 4 and 5, these interfaces being highly echogenic.

It will also be observed here that the therapy device is preferably enclosed inside a membrane 50 (FIGS. 5–6) filled with an acoustic coupling fluid 52 which for example is water, enabling acoustic waves to be transmitted to the target, for example tumor T inside organ O, which here, in FIGS. 4 and 5, is the prostate PR.

In the framework of FIGS. 4 and 5, which more particularly concern treatment of the prostate, the interface I that is being monitored is the rectal wall R as, when focused ultrasound is used with the focal point F of focused therapy transducer 14 located very close to the rectal wall W. This presents a risk to the patient P as incorrect positioning of therapy device 12 could lead to destruction of the rectal wall W with obvious serious consequences. It is thus extremely important to permanently monitor the position of the rectal wall with respect to the therapy transducer 14.

Monitoring is done in the following manner. Monitoring transducer 16, which here constitutes the central portion of therapy transducer 14, issues a brief pulse, for example, having a 1 is width at a frequency of 2.25 MHz, supplied by pulse generator 32 (FIG. 3), the echo being received by the movement detecting device 28 where it is processed by amplifier 34 and detector 36, the latter analyzing the echo and comparing it with a reference echo.

The manner in which this comparison is achieved can be understood with reference to FIG. 5 where the shape of the echo signal as a function of time T is shown on the x-axis, the y-axis showing the signal amplitude A. The echo signal E following transmission of a pulse at instant O from monitoring transducer 16 first indicates passage through a feebly echogenic region $E_e$ due to the coupling water, such as water e, and then corresponds to an encounter with the interface I constituted by the rectal wall and, specifically, the wall of the prostate PR, the latter being the organ O to be treated. This interface I constituted by rectal wall W is highly echogenic and gives rise to a reference echo $E_r$, which is the echo that will be monitored in the framework of this invention. It will be noted that this echo is encountered at a time $t_I$ from the moment the signal was generated, corresponding to travel over a distance $D_I$ between monitoring transducer 16 and rectal wall W, in the monitoring zone of monitoring transducer 16.

It will be understood that when the patient moves, this will also lead to the organ O of FIGS. 4 and 5, which is here the prostate PR, moving with a corresponding change in the distance $D_I$ between the monitoring transducer 16 and the rectal wall W.

In a first embodiment of the invention, one can simply compare the instant $t_I$ at which the echo $E_I$ arrives at with a reference echo, which can be the echo received just prior to, or at the beginning of, treatment. Alternately, one can compare the distance travelled by the return echo with the distance measured by distance measuring means prior to the commencement of treatment. When the time $t_I$ deviates from the reference echo time, this signifies that the distance $D_I$ has changed with respect to the initially measured distance between the monitoring transducer 16 and the rectal wall, meaning that the patient has moved. In this case, the detection and analysis device 36 may issue a command to output unit 40 to supply an alarm signal and/or to issue a command to the translatory and/or rotational movement control means for therapy device 12 incorporating monitoring device 16, whereby the echo from interface I may once again be brought to appear at a time $t_I$ identical or close to the time of appearance of the reference echo.

It can thus be noted that provision can be made to either trigger an alarm signal 42 or issue commands to move the therapy transducer 16 only in the case where the time $t_I$ at which the echo from interface $E_I$ occurs is below or above a predetermined value for the reference echo time.

It can thus be noted that with the invention, monitoring of the patient's movement can be automated as can correction of the position of therapy device 12 during treatment.

Provision can also be made not only to calculate the time $t_I$ of the echo from interface $E_I$, but also the distance $D_I$ corresponding to the substantially constant known speed of sound in the acoustic coupling fluid and in tissue, this distance $D_I$ together with the time $t_I$ being able to be displayed on a screen permits the practitioner to follow the progress of treatment with an enhanced degree of safety.

FIG. 6 shows a further embodiment of the invention concerning here the treatment of nodules N of the thyroid gland. The same reference numerals and symbols as those used in FIGS. 4 and 5 have been used to indicate identical elements.

Here, the interface that it is particularly important to monitor occurs at the trachea, this interface being identified by symbol $I_2$ on FIG. 6. The interface at the trachea also generates a pronounced echo $E_{I2}$ which can be clearly seen as a strong echo signal on FIG. 6. Before this interface at the trachea $I_2$, there is obviously a first interface $I_1$ constituted by the skin S of the patient P but here, this interface which furthermore generates a first strong echo $E_{I1}$ is of little significance compared to the interface at the trachea $I_2$.

When treating the thyroid, it is the interface $I_2$ that will be used for measuring the time $t_{I2}$ for the echo to appear, this time corresponding to the distance $D_{I2}$ between the monitoring transducer and the interface $I_2$ at the trachea.

Monitoring is done in the same way as in FIGS. 4 and 5. Changes in the time $t_{I2}$ at which the echo $E_{I2}$ appears, when compared to the reference expected time of appearance, makes it possible to set off an alarm signal 42 via the output unit 40 (FIG. 3) and/or to command a change of position of therapy device 12 via the control unit 22 and the translatory and/or rotational displacement 20.

The invention thus makes it possible to resolve all the problems discussed above, and to obtain all the technical advantages derived therefrom, as will be readily appreciated by those skilled in the art.

Obviously, the invention includes all means that constitute technical equivalents to those described, as well as the various combination thereof.

For example, monitoring transducer 16 operating in A-mode can also be set to transmit a continuous signal, the echoes being recorded continuously thus making it possible to provide visual monitoring of movements made by the patient p.

Additionally, this invention covers all features that appear to be novel vis-a-vis any state of the art, given in the description incorporating FIGS. 1 to 6 which constitute an integral part thereof, and in the claims.

What is claimed is:

1. A method of monitoring a position of a patient during a therapy session, the method comprising the steps of:
   providing an A-mode echography device having an A-mode echography transducer;
   activating the A-mode echography transducer to determine a distance between the A-mode transducer and a target structure of the patient to be monitored, the target structure having a predetermined relationship to an organ of the patient to be treated;
   providing a therapy transducer, the therapy transducer operatively coupled to the A-mode echography transducer; and
   determining whether the therapy transducer is within a predetermined distance relative to the organ of the patient by monitoring the distance between the A-mode transducer and the target structure.

2. The method according to claim 1, wherein the distance between the therapy transducer and the organ of the patient is modified as a function of movements detected between the A-mode echography transducer and the organ of the patient.

3. The method according to claim 1, wherein said A-mode echography device interrupts operation of the therapy transducer if it is detected that movements of the patient relative to the A-mode echography transducer are greater than a predefined amount.

4. The method according to claim 1, wherein said A-mode echography device carries out real time control of the position of the therapy transducer, with respect to a predetermined reflecting contour.

5. A method for monitoring and treating an organ of a patient during a therapy session, the treatment of the organ provided by a therapy device having a therapy transducer, the method comprising the steps of:
   a) providing an ultrasound monitoring transducer operating in A-mode, the monitoring transducer acoustically coupled to a target structure, the target structure having a predetermined relationship to the organ to be monitored;
   b) exciting the ultrasound monitoring transducer with a signal in the form of a pulse, the pulse applied during a time interval between the application of therapy by the therapy transducer;
   c) receiving echoes of the signal produced by the monitoring transducer;
   d) transforming the received echoes into an electrical signal;
   e) locating, in the electrical signal corresponding to the received echoes, the position of the target structure to determine a measured distance from the monitoring transducer to the target structure, the target structure defining a highly echogenic interface relative to the organ to be monitored and treated;
   f) comparing the distance measured between the monitoring transducer and the target structure with a reference distance, the reference distance corresponding to the distance between the highly echogenic interface in contact with a wall of a balloon means corresponding to the ultrasound therapy transducer; and
   g) transmitting a control signal to a control device operative to selectively control the position of the therapy transducer in response to the change in distance between the monitoring transducer and the target structure relative to the reference distance.

6. The method according to claim 5, wherein the control device triggers an alarm when information is transmitted to the control device indicating that a change in the measured distance is greater than a predetermined amount.

7. The method according to claim 5, wherein said control device performs real time closed-loop control of the position of said therapy device as a function of the movements of said patient with respect to a reflecting contour of said patient, said reflecting contours having a known relationship to the organ of the patient.

8. The method according to claim 5 wherein said ultrasound monitoring transducer operating in A-mode is mechanically linked to said therapy transducer.

9. The method according to claim 5 wherein said therapy device comprises at least one ultrasound therapy transducer providing therapy using focused ultrasound.

10. The method according to claim 5 wherein said ultrasound therapy transducer is arranged inside balloon means filled with an acoustic coupling fluid.

11. The method according to claim 5 wherein if said measured distance is smaller than said reference distance, the control device controls said therapy transducer to increase a distance between the therapy transducer and the target structure to be treated while if said measured distance is greater than said reference distance, the control device controls said therapy transducer to decrease a distance between the therapy transducer and the target structure to be treated.

12. The method according to claim 5 wherein said ultrasound therapy transducer is a focused ultrasound therapy transducer integrated into an endocavital probe for providing treatment of the prostate or the thyroid.

13. The method for monitoring and treating an organ of a patient during a therapy session, the treatment of the organ provided by a therapy device having a therapy transducer, the method comprising the steps of:
   a) providing an ultrasound monitoring transducer operating in A-mode, the monitoring transducer acoustically coupled to a target structure, the target structure having a predetermined relationship to the organ to be monitored;
   b) exciting the ultrasound monitoring transducer with a signal in the form of a pulse, the pulse applied during a time interval between application of therapy by the therapy transducer;
   c) receiving echos of the signal produced by the monitoring transducer;
   d) transforming the receive echoes into an electrical signal;
   e) locating, in the electrical signal corresponding to the receive echoes, the position of the target structure to determine a measured distance from the monitoring transducer to the target structure, the target structure defining a highly echogenic interface relative to the organ to be monitored;
   f) comparing the distance measured between the monitoring transducer and the target structure, with a reference distance; and
   g) transmitting a control signal to a control device operative to selectively control the position of the therapy transducer in response to change in distance between the monitoring transducer and the target structure relative to the reference distance.

14. The method according to claim 13 wherein the control device triggers an alarm when information is transmitted to the control device indicating a change in the measured distance cannot be determined.

15. The method according to claim 13 wherein the control device triggers an alarm when information is transmitted to the control device indicating a change in the measured distance is greater than a predetermined amount.

16. The method according to claim 13 wherein the monitoring transducer received the echos reflected from the target structure, the target structure being at least one of a rectal wall during prostate treatment and a trachea during thyroid treatment.

17. The method according to claim 16 wherein the target structure is a reflecting contour having a predetermined relationship relative to the organ of the patient to be treated.

18. The method according to claim 13 wherein said ultrasound monitoring transducer operating in A-mode is mechanically linked to said therapy transducer.

19. The method according to claim 13 wherein said therapy device comprises at least one ultrasound therapy transducer providing therapy using focused ultrasound.

20. The method according to claim 13 wherein said ultrasound therapy transducer is arranged inside balloon means filled with an acoustic coupling fluid.

21. The method according to claim 13 wherein if the measured distance between the monitoring transducer and the target structure is smaller than the reference distance, the control device increases a distance between the therapy transducer and the organ to be treated, while if the measured distance between the monitoring transducer and the target structure is greater than the referenced distance, the control device controls decreases the distance between the therapy transducer and the organ to be treated.

22. The method according to claim 13 wherein the ultrasound therapy transducer is a focused ultrasound therapy transducer integrated into an endocavital probe for providing treatment of the prostate or the thyroid.

23. A therapy apparatus for treating an organ of a patient, the apparatus comprising:

at least one ultrasound therapy transducer and at least one ultrasound monitoring transducer, the monitoring transducer operating in A-mode;

the ultrasound monitoring transducer operatively coupled to an electronic circuit for processing A-mode signals produced by the ultrasound monitoring transducer;

means for coupling the ultrasound monitoring transducer to transmit a pulse signal, the pulse signal causing an echo to be received by the ultrasound monitoring transducer, the echo caused by a reflection of the pulse signal from a target structure, the target structure defining an echogenic interface having a predetermined relationship relative to the organ to be monitored;

means for comparing the echo received with a reference echo and transmitting the result of the comparison to a control device; and the control device coupled to the means for comparing and coupled to the ultrasound therapy transducer, the control device receiving the result of the comparison and controlling the ultrasound therapy transducer in response thereto.

24. The apparatus according to claim 23, wherein said control device triggers an alarm in response to the result of the comparison.

25. The apparatus according to claim 23, wherein said control device performs real time closed-loop control of the position of said therapy transducer as a function of the movements of the patient, the control device controlling the position of the therapy transducer in real time with respect to a predetermined reflecting contour of said patient, said reflecting contour having a known relationship to the organ of the patient to be treated.

26. The apparatus according to claim 23 wherein said ultrasound therapy transducer is of the focused type.

27. The apparatus according to claim 26, wherein said focused-type therapy transducer is linked to means for supplying an electronic signal providing variable focusing.

28. The apparatus according to claim 27, wherein said control device provides closed-loop control of the focal length of said therapy transducer as a function of the movements of said patient, during the course of therapy.

29. The apparatus according to claim 23, wherein both said ultrasound therapy transducer and said A-mode monitoring transducer are integrated into an endocavital probe.

30. The apparatus according to claim 23, wherein said therapy apparatus includes means for continuously recording the echoes created by said monitoring transducer operating in A-mode.

31. The apparatus according to claims 23, wherein said ultrasound monitoring transducer is mechanically linked to said therapy device.

32. The apparatus according to claim 23, wherein said therapy device comprises at least one ultrasound therapy transducer providing therapy using focused ultrasound, said ultrasound therapy transducer enclosed within a balloon means filled with an acoustic coupling fluid.

33. The apparatus according to claim 23, wherein said apparatus is operative to treat the prostate or the thyroid.

34. A method for monitoring and treating an organ of a patient during a therapy session, the treatment of the organ provided by a therapy device having a therapy transducer, the method comprising the steps of:

a) providing an ultrasound monitoring transducer operating in A-mode, the monitoring transducer acoustically coupled to a target structure, the target structure having a predetermined relationship to the organ to be monitored;

b) exciting the ultrasound monitoring transducer with a signal in the form of a pulse, the pulse applied during a time interval between the application of therapy by the therapy transducer;

c) receiving echoes of the signal produced by the monitoring transducer;

d) transforming the received echoes into an electrical signal;

e) locating, in the electrical signal corresponding to the received echoes, the position of the target structure to determine a measured distance from the monitoring transducer to the target structure, the target structure defining a highly echogenic interface relative to the organ to be monitored and treated; and f) comparing the distance measured between the monitoring transducer and the target structure with a reference distance, the reference distance corresponding to the distance between the highly echogenic interface in contact with a wall of a balloon means corresponding to the ultrasound therapy transducer.

* * * * *